United States Patent
Chalyt et al.

(10) Patent No.: US 6,749,739 B2
(45) Date of Patent: Jun. 15, 2004

(54) DETECTION OF SUPPRESSOR BREAKDOWN CONTAMINANTS IN A PLATING BATH

(75) Inventors: Gene Chalyt, Washington Township, NJ (US); Peter Bratin, Flushing, NY (US); Michael Pavlov, Fairlawn, NJ (US); Alex Kogan, Carlstadt, NJ (US); Michael James Perpich, Hackensack, NJ (US)

(73) Assignee: ECI Technology, Inc., East Rutherford, NJ (US)

( * ) Notice: Subject to any disclaimer, the term of this patent is extended or adjusted under 35 U.S.C. 154(b) by 86 days.

(21) Appl. No.: 10/266,006

(22) Filed: Oct. 7, 2002

(65) Prior Publication Data

US 2004/0065561 A1 Apr. 8, 2004

(51) Int. Cl.[7] .......................... G01N 27/26; C25D 21/12
(52) U.S. Cl. ....................... 205/788.5; 205/81; 205/787; 204/434
(58) Field of Search ................................ 205/775, 787, 205/788.5, 81; 204/405, 434

(56) References Cited

U.S. PATENT DOCUMENTS 4,628,726 A * 12/1986 Heikkila et al. ............ 73/61.53
6,508,924 B1 * 1/2003 Gomez et al. ................ 205/81
6,572,753 B2 * 6/2003 Chalyt et al. ................. 205/81

OTHER PUBLICATIONS

Freitag et al, Determination of the Individual Additive Components in Acid Copper Plating Baths, Plating Surf. Fin. 70(10), pp. 55–60, 1983.*

Haak et al, Cyclic Voltammetric Stripping Analysis of Acid Copper Sulfate Plating Baths, Part 2: Sulfoniumalkane-sulfonate–Based Additives, Plating Surf. Fin. 69(3), pp. 62–66, 1982.*

* cited by examiner

Primary Examiner—Kaj K. Olsen
(74) Attorney, Agent, or Firm—D. Morgan Tench

(57) ABSTRACT

Relative concentrations of active suppressor additive species and suppressor breakdown contaminants in an acid copper electroplating bath are determined by cyclic voltammetric stripping (CVS) dilution titration analysis using two negative electrode potential limits. The analysis results for the more negative potential limit provide a measure of the suppressor additive concentration alone since the suppressor breakdowvn contaminants are not effective at suppressing the copper deposition rate at the more negative potentials. The analysis results for the less negative potential limit provide a measure of the combined concentrations of the suppressor additive and the suppressor breakdown contaminants. Comparison of the results for the two analyses yields a measure of the concentration of the suppressor breakdown contaminants relative to the suppressor additive concentration.

27 Claims, 4 Drawing Sheets

DETECTION OF SUPPRESSOR BREAKDOWN CONTAMINANTS IN A PLATING BATH

CROSS-REFERENCE TO RELATED APPLICATIONS

This application is related to U.S. patent application Ser. No. 09/968,202, filed Oct. 1, 2001, to Chalyt et al., which is assigned to the same assignee.

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52(1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain additives of more than one type, as well as other organic and inorganic addition agents. The suppressor additive may be comprised of more than one chemical species and generally involves a range of molecular weights.

Acid copper sulfate baths have functioned well for plating the relatively large surface pads, through-holes and vias found on printed wiring boards (PWB's) and are currently being adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p.32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process has shrunk below 0.2 $\mu$m, it has become necessary to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. In order to attain good bottom-up filling and avoid overplating of ultra-fine chip features, the concentrations of all three additives must be accurately analyzed and controlled.

The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. 70$^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. patent application Ser. No. 09/968,202 to Chalyt et al. (filed Oct. 1, 2001).

Analysis for the suppressor additive typically involves generation of a calibration curve by measuring the CVS rate parameter $A_r$ in a supporting electrolyte, termed $A_r(0)$, and after each standard addition of the suppressor additive. The supporting electrolyte typically has the same organic content as the plating bath being analyzed but does not contain organic additives. The $A_r$ parameter may be plotted against the suppressor concentration directly, or be normalized as $A_r/A_r(0)$ to minimize measurement errors associated with changes in the electrode surface, background bath composition, and temperature. For the suppressor analysis itself, $A_r$ is first measured in the supporting electrolyte and then after each standard addition of a known volume fraction of the plating bath sample to be analyzed. The suppressor concentration may be determined from the $A_r$ or $A_r/A_r(0)$ value for the measurement solution (supporting electrolyte plus a known volume fraction of plating bath sample) by interpolation with respect to the appropriate calibration curve ("response curve analysis"). Alternatively, the suppressor concentration may be determined by the "dilution titration" method from the volume fraction of plating bath sample (added to the supporting electrolyte) required to decrease $A_r$ or $A_r/A_r(0)$ to a predetermined value, which may be a specific numerical value or a minimum value corresponding to substantially maximum suppression [W. O. Freitag, C. Ogden, D. Tench and J. White, Plating Surf. Fin. 70(10), 55 (1983)]. Note that the effects of the anti-suppressor and leveler additives on the suppressor analysis are typically small but can be taken into account by utilizing a background electrolyte (instead of the supporting electrolyte) containing the concentrations of these additives measured or estimated to be present in the plating bath being analyzed.

Suppressor additives in acid copper baths are typically supplied as long-chain polymers (e.g., polyethylene glycol or polypropylene glycol) of high molecular weight (>5000) but the polymer chains are cleaved during copper electrodeposition so that chemically similar species of lower molecular weight are produced. These lower-molecular-weight suppressor breakdown products are less effective at suppressing copper electrodeposition, and those with sufficiently low molecular weight represent contaminants that interfere with the electrodeposition process. To obtain acceptable electrodeposits, the concentrations of such suppressor breakdown contaminants must be maintained at low levels in the plating bath. This is normally accomplished by a bleed and feed operation in which a portion of the plating bath is continuously or periodically removed and replaced with fresh plating solution. A method is needed for monitoring the buildup of suppressor breakdown products so that the bleed and feed rates can be optimized to ensure acceptable electrodeposits, while minimizing consumption of expensive plating solution and generation of environmentally objectionable waste.

Available methods for detecting suppressor breakdown contaminants in acid copper baths are inadequate. The normal CVS standard addition or dilution titration analysis involving electrode potential cycling between fixed positive and negative limits yields the effective suppressor concentration but does not distinguish between high and low molecular weight species. Likewise, total organic carbon analysis does not provide information about the individual species present in the plating bath. The overall organic contaminant level in acid copper baths can also be detected via the diffusion-limited oxidation current at a platinum rotating disk electrode. This approach is widely used (in conjunction with CVS analysis) to detect contaminants in printed wiring board (PWB) plating baths but is not sensitive enough to detect the low levels of contaminants that interfere with plating of trenches and vias in the Damascene wafer plating process.

SUMMARY OF THE INVENTION

The present invention provides a sensitive method for determining the relative concentrations of active suppressor additive species and suppressor breakdown contaminants in an acid copper electroplating bath. In this method, the volume fraction of the plating bath added to the bath supporting electrolyte (or a background electrolyte) required to produce a predetermined decrease in the copper electrodeposition rate is determined for two predetermined copper deposition potentials or potential ranges. The volume fraction required for the more negative potential or potential range provides a measure of the concentration of the active suppressor additive since the suppressor breakdown contaminants are not effective at suppressing the copper deposition rate at the more negative potentials. The volume fraction required for the less negative potential or potential range provides a measure of the combined concentrations of the active suppressor additive and the suppressor breakdown contaminants A comparison (mathematical difference or ratio, for example) of the ,measured volume fractions for the two potentials or potential ranges yields the concentration of the suppressor breakdown contaminants relative to the active suppressor additive concentration. Both of these concentrations are averaged (or effective) concentrations since the active suppressor additive and the breakdown contaminants are each comprised of species having a range of molecular weights. The molecular weight ranges for the species detected depend on the specific electrode potentials used for the analysis.

In a preferred embodiment, CVS (or CPVS) dilution titration analyses are performed on an copper plating bath using two different negative potential limits. For these analyses, the CVS rate parameter ($A_r$) is first measured in the supporting electrolyte, termed $A_r(0)$, and then after each standard addition (to the supporting electrolyte) of a known, volume fraction of the plating bath solution being analyzed. The volume fraction of plating bath solution corresponding to a predetermined value of $A_r$ or $A_r/A_r(0)$ provides a measure of the active suppressor concentration for the more negative potential limit, and the suppressor breakdown contaminant concentration plus the active suppressor concentration for the less negative potential limit. The predetermined value of $A_r$ or $A_r/A_r(0)$ may be a specific numerical value or a minimum value corresponding to substantially maximum suppression of the copper deposition rate. A calculated parameter based on a mathematical relationship between the solution volume fractions for the two potential limits (e.g., the ratio or difference) is used as a relative measure of the suppressor breakdown contaminant concentration. Since suppressor polymer chains of various lengths are produced during the copper electrodeposition process, calibration curves of the calculated parameter versus suppressor breakdown contaminant concentration are of limited use. On the other hand, the electrode potential limit used for the suppressor breakdown contaminant analysis may be adjusted to vary the molecular weight range of the species detected.

The analysis of the present invention is readily performed by repeating the normal CVS or CPVS suppressor additive analysis using a less negative cathodic potential limit (to determine the relative concentration of suppressor breakdown contaminants). For the CVS dilution titration approach, known volumes of the plating bath being analyzed are added to a known volume of the supporting electrolyte (or a background electrolyte) until $A_r$ or $A_r/A_r(0)$ reaches a minimum value corresponding to maximum suppression of the copper deposition rate, or $A_r$ is decreased to a predetermined percentage (or fraction) of the $A_r(0)$ value. The endpoint for the titration is typically the point at which maximum suppression is attained, or the $A_r$ value reaches 50% of the $A_r(0)$ value. For the response curve approach, the relative suppressor and suppressor breakdown contaminant concentrations are determined from the $A_r$ or $A_r/A_r(0)$ values measured at the two negative potential limits for a measurement solution (supporting electrolyte plus a known volume fraction of plating bath sample) by interpolation with respect to a suppressor calibration curve.

The present invention enables suppressor additive breakdown contaminants in acid copper baths to be analyzed and controlled so as to ensure acceptable copper electrodeposits while minimizing consumption of expensive plating solution and generation of environmentally objectionable waste. Such optimized plating bath performance may be attained via appropriate adjustments in the additive bleed and feed rates, and/or as-needed replacement of all or part of the plating bath. The present invention may also be used to determine the need for carbon treatment, which may be used to remove bath contaminants in some cases. In addition, the present invention may be applied to baths, employing polymeric additives, used to electrodeposits other metals, tin, tin-lead, nickel or cobalt, for example.

Further features and advantages of the invention will be apparent to those skilled in the art from the following detailed description, taken together with the accompanying drawings.

DETAILED DESCRIPTION OF THE INVENTION

Figure 1:
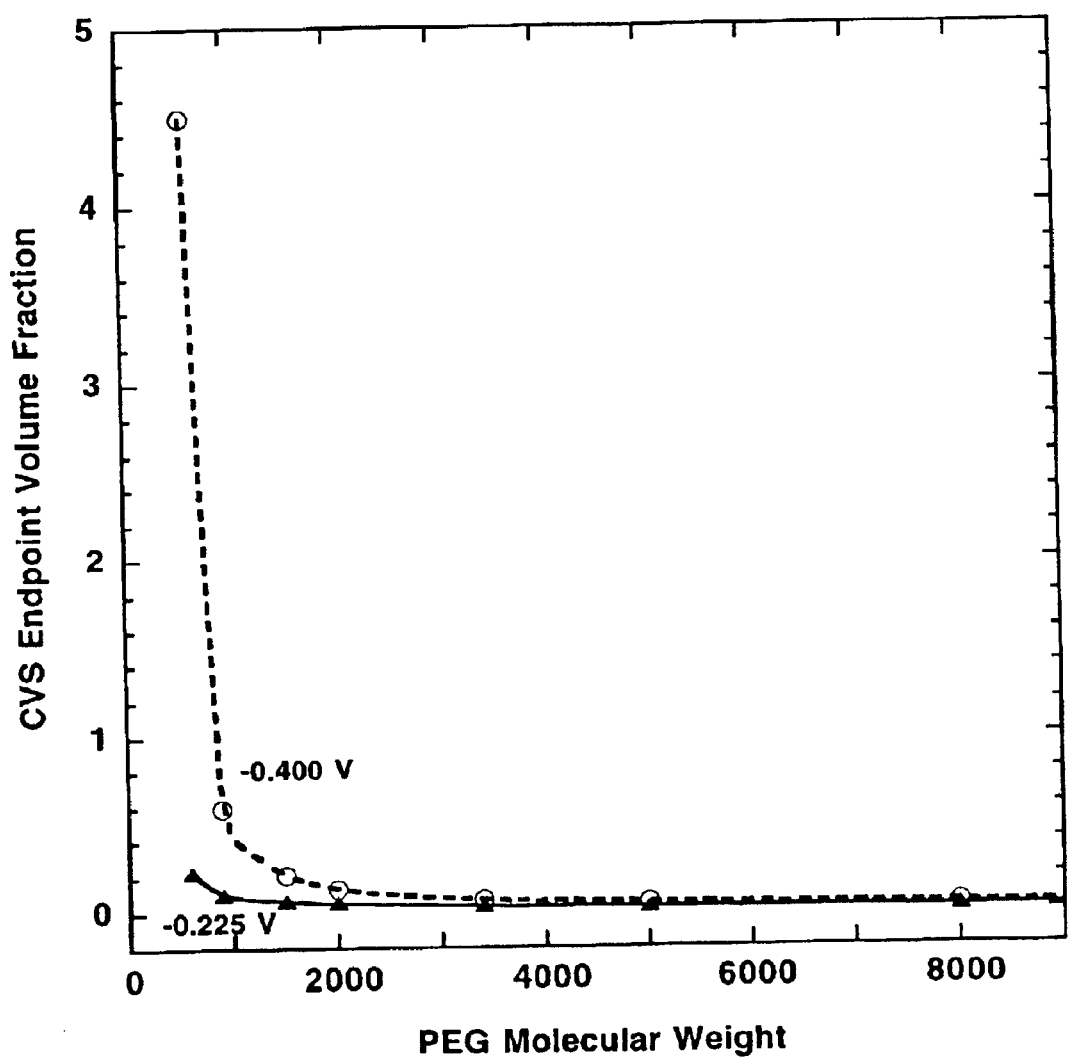
FIG. 1 shows the effect of PEG molecular weight on the volume fraction of 10 $\mu$M PEG solutions added to the supporting electrolyte required for 50% suppression of the CVS rate parameter ($A_r$) measured with negative potential limits of −0.225 and −0.400 V vs. SSCE/M.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results. As used in this document, the terms "electroplating", "plating" and "electrodeposition" are equivalent. A "plating bath" contains organic additives whose concentrations are controlled within ranges, whereas the corresponding "supporting electrolyte" has substantially the same inorganic composition but no organic additives, and a "background electrolyte" is the supporting electrolyte with known amounts of organic additives added. The term "plating solution" encompasses the terms "background electrolyte" and "supporting electrolyte". The symbol "M" means molar concentration.

In this document, the term "standard addition" generally means addition of a known volume of a plating bath sample or of an additive solution to a known volume of a supporting electrolyte or background electrolyte. Such standard addition does not change the name of the plating solution so that a reduction in the plating rate may be measured for a given solution (before and after the standard addition). The "volume fraction" is the volume of added plating bath sample or additive solution divided by the total volume of the solution after the addition. The term "standard addition" also encompasses addition of a known weight of a solid additive species to a known volume of a supporting electrolyte or background electrolyte. Calibration data are typically handled as calibration curves or plots but such data may be tabulated and used directly, especially by a computer, and the terms "curve" or "plot" include tabulated data.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The present invention provides a method for determining the relative concentrations of active suppressor additive species and suppressor breakdown contaminants in acid copper electroplating baths. Polyethylene glycol and polypropylene glycol are the most commonly used suppressor additives for acid copper baths but the method of the present invention may also be applied to analysis of other polymeric additives, including polyalkylene oxides and other polyalkylene glycols. Acid copper sulfate is the most widely used acid copper bath but the analysis of the present invention may also be applied to acid copper baths employing a variety of anions, including sulfate, chloride, bromide, iodide, fluoroborate, sulfamate, alkylsulfonate, and mixtures thereof. In addition, the present invention may be applied to other types of plating baths employing polymeric additives that undergo cleavage during bath operation. Such baths might include those used for plating of tin, tin-lead, nickel or cobalt for example.

In the method of the present invention, the metal electrodeposition rate is measured for two predetermined electrode potentials in a known volume of the supporting electrolyte (or a background electrolyte) before and after addition of known volumes of the plating bath being analyzed. The predetermined electrode potentials may be fixed potentials or potential ranges (which may overlap). For each of the predetermined potentials, the volume fraction of the plating bath required to reduce the metal electrodeposition rate to a predetermined endpoint value is determined. This endpoint may correspond to a specific value for an electrodeposition rate parameter or to substantially maximum suppression in the electrodeposition rate, or a predetermined fraction thereof. At the more negative metal deposition potential, the suppressor breakdown contaminants are not effective at suppressing the metal deposition rate so that the endpoint volume fraction provides a measure of the active suppressor additive concentration alone. The endpoint volume fraction for the less negative potential provides a measure of the combined concentrations of the active suppressor additive and the suppressor breakdown contaminants. A comparison of the plating bath volume fractions for the two endpoints yields the concentration of the suppressor breakdown contaminants relative to the active suppressor additive concentration.

The relative concentration of the suppressor breakdown contaminants is preferably expressed as the mathematical difference or ratio of the endpoint volume fractions measured for the two negative electrode potential limits. A wide variety of other mathematical expressions may be used. Although the difference parameter has concentration units, this has little meaning with respect to the absolute concentration of the suppressor breakdown contaminants, which are typically comprised of polymer chains of varying lengths. Consequently, calibration curves for suppressor breakdown contaminants are of limited use for process control. Typically, the value of a relative concentration parameter determined by the method of the present invention is correlated with the deposit quality so as to define an acceptable relative contaminant concentration range for the specific plating process. Periodic measurements of this parameter are then used as feedback for adjusting bleed and feed rates, or deciding to replace or carbon treat the bath to remove the contaminants. The molecular weight range of the suppressor breakdown contaminants detected may be adjusted via the electrode potential limit used for the analysis.

The metal deposition rate for the method of the present invention is preferably determined by cyclic voltammetric stripping (CVS) or cyclic pulse voltammetric stripping (CPVS). The latter is also called cyclic step voltammetric stripping (CSVS). As used in this document, the term "cyclic voltammetric stripping" or "CVS" implicitly includes the CPVS method, which is a variation of the CVS method. Likewise, the term "CVS rate parameter" includes the analogous CPVS voltammetric rate parameters.

In the CVS method, the potential of an inert working electrode, typically platinum, is cycled in a plating solution at a constant rate between fixed potential limits so that a metal is alternately electrodeposited on the electrode surface and anodically stripped back into the solution. Preferably, a rotating disk electrode configuration is used for the working electrode to control solution mass transport so as to improve the sensitivity and reproducibility of the analysis results. The metal deposition rate is preferably measured via the metal stripping peak area at a constant electrode rotation rate ($A_r$) but may also be determined from the stripping peak height, or from the electrode impedance, current (including average current), or integrated current (i.e., charge) measured for a predetermined cathodic potential or potential range (with or without electrode rotation). All of these rate parameters provide a relative measure of the metal electrodeposition rate that can readily be used for comparisons only when the measurement conditions are the same. Improved reproducibility and accuracy may be provided by using the normalized CVS rate parameter, $A_r/A_r(0)$, which is the ratio of the stripping peak area for a plating solution after a standard addition to that for plating solution without additions.

For CVS analyses, a plurality of potential cycles is typically employed to condition the working electrode surface so as to provide reproducible results. In this case, data are accepted only when a steady-state condition is reached, as indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may be comprised of any suitable electrically conducting material that is stable in the plating solution under the conditions used for the voltammetric analysis but is preferably comprised of a noble metal, for example, platinum, iridium, gold, osmium, palladium, rheniun, rhodium, ruthenium, and alloys thereof. Other oxidation-resistant metals and alloys, stainless steel, for example, may also be used as working electrode materials. A typical CVS rotating disk electrode is comprised of a platinum metal disk (3–5 mm diameter), with an electrical contact wire on the backside, embedded flush with one end of an insulating plastic cylinder (10–20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100–5000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be a reactive metal (copper or a copper alloy, for example) or an inert metal. Depolarizers (sulfur or phosphorus, for example) may be included in the counter electrode to facilitate dissolution of the metal so as to avoid breakdown of the plating solution. Practically any electrical conductor that resists oxidation and reduction in the plating solution may be used as an inert counter electrode, including metals, alloys and conducting oxides (mixed titanium-ruthenium oxide, for example). A preferred inert counter electrode material is 316 stainless steel, which is highly oxidation-resistant and relatively inexpensive but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Metal deposition rates according to the present invention may also be measured by methods other than CVS, including those based on measurements of the ac impedance of the cathode, for example. The same electrode materials and configurations can be used for such alternative methods. Although the precision and reproducibility of the analysis might be degraded, current measurements reflecting the metal deposition rate could also be made at a stationary electrode and/or without potential cycling. If a stationary working electrode is used for the suppressor breakdown contaminant analysis of the present invention, the hydrodynamic conditions at the electrode surface are preferably controlled, by stirring or pumping the solution, for example.

In a preferred embodiment of the present invention, CVS dilution titration analyses are performed on a copper plating bath sample using two different negative potential limits. For these analyses, the CVS rate parameter ($A_r$) is first measured in the supporting electrolyte alone, termed $A_r(0)$, and then in the supporting electrolyte after each standard addition (to the supporting electrolyte) of a known volume fraction of the plating bath solution being analyzed. The value of $A_r$ or $A_r/A_r(0)$ is plotted vs. the volume fraction of plating bath sample added to the supporting electrolyte. One suitable endpoint for the CVS dilution titration is the volume fraction of added plating bath at which $A_r$ or $A_r/A_r(0)$ reaches a minimum value, $A_r(\min)$ or $A_r(\min)/A_r(0)$, corresponding to substantially maximum copper deposition rate suppression. This endpoint is approached asymptotically and may be difficult to detect reproducibly with high accuracy. A preferred endpoint is the volume fraction of added plating bath at which the $A_r$ value is decreased to a predetermined percentage (typically 50%) of the $A_r(0)$ value. Another preferred endpoint corresponds to a specified fraction or percentage of the maximum suppression in the copper deposition rate. For example, the endpoint for 50% suppression in the $A_r$ value would correspond to 0.5 $[A_r(0)+A_r(\min)]$. These preferred endpoints provide better accuracy since they occur on the steep portion of the $A_r$ vs. plating bath volume fraction curve. A variety of other suitable endpoints will be apparent to those skilled in the art.

In an alternative embodiment, CVS response curve analyses are performed on a plating bath sample using two different negative potential limits. In this case, the active suppressor concentration is determined from the $A_r$ or $A_r/A_r(0)$ value for a measurement solution (supporting electrolyte plus a known volume fraction of plating bath sample) by interpolation with respect to a suppressor calibration curve of $A_r$ or $A_r/A_r(0)$ measured at the more negative potential vs. suppressor concentration or volume fraction. Comparison of the $A_r$ or $A_r/A_r(0)$ value measured for the measurement solution at the less negative potential with the calibration curve for $A_r$ measured at the more negative potential yields a relative measure of the suppressor breakdown contaminant level. This embodiment also involves measuring the reduction produced by standard addition of a plating bath sample on the metal electrodeposition rate measured for a plating solution at two negative potentials or potential ranges.

The effects of anti-suppressor and leveling additives in acid copper baths on the analysis of the present invention are typically small since the suppressor effect is generally much stronger at the low additive concentrations resulting from the standard additions involved in the analysis. If necessary, the effects of interfering additives can be reduced by employing a background electrolyte (instead of the supporting electrolyte) containing these additives at the concentrations measured or estimated to be present in the plating bath.

The composition of acid copper electroplating baths varies greatly depending on the type of bath and the supplier. High-acid baths typically contain 40–100 g/L copper sulfate, 140–240 g/L sulfuric acid and 25–100 ppm chloride ion. Low-acid baths typically contain 125–200 g/L copper sulfate, 1–40 g/L sulfuric acid and 25–100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Since chloride exerts a strong effect on the functioning of suppressor additives used in acid copper baths, its concentration should, if necessary, be adjusted to be within the appropriate range (typically, 25 to 100 ppm) in the plating bath sample being analyzed, and in the background and supporting electrolytes used for the analysis. Variations in the chloride, sulfuric acid and copper ion concentrations within the ranges recommended by the bath supplier usually have a negligible effect on the suppressor and suppressor breakdown contaminant analysis results and typically need to be adjusted in measurement solutions only for analyses requiring very high accuracy.

Copper electrodeposition rate measurements are preferably made at a constant temperature (within to ±0.5° C.) since errors resulting from temperature variations may be significant. Acid copper baths are typically operated at ambient temperature but measurements may be made at a higher or a lower temperature. The accuracy of CVS rate parameter measurements may be improved by employing a slightly elevated solution temperature (3° or 4° C. above room temperature, for example) that can be more consistently maintained.

Best results for the analysis of the present invention are provided by optimizing the CVS measurement parameters for the particular bath type and additive system employed. The key CVS measurement parameters and their typical ranges for acid copper baths include the electrode rotation rate (100–10,000 rpm), potential scan rate (10–1000 mV/s), negative potential limit (−0.05 to −0.5 V vs. SSCE) and positive potential limit (1.4 to 1.8 V vs. SSCE). A positive potential limit of relatively high voltage (in the oxygen evolution region) is used so that organic species adsorbed on the electrode surface are removed by electrochemical oxidation on each cycle, which provides more reproducible results. Additional CPVS measurement parameters include the potentials and hold times for the pulses or steps used.

Optimization of the CVS measurement parameters typically involve variations in the negative potential limit and/or the potential scan rate, which determine the amount of metal deposited on the electrode and thus the sensitivity of the rate parameter to additive effects. For example, a more negative potential limit or slower scan rate may be needed to deposit sufficient metal for the suppressor analysis when the suppressor effect is relatively strong. The potential scan rate and limits also influence the sensitivity of the rate parameter to additives by affecting additive adsorption/desorption processes, as well as the relative magnitudes of charging and faradaic currents. Another key optimization parameter is the electrode rotation rate, which determines the rate at which additive species are replenished at the electrode surface as they are consumed during metal electrodeposition. Typically, the rotation rate is increased for detection of an additive species present at relatively low concentration.

For the suppressor breakdown contaminant analysis of the present invention, the values of the two negative CVS voltage limits are preferably adjusted to provide good separation between the effects of the active suppressor and the breakdown contaminants. Generally, the more negative limit is adjusted so that the CVS rate parameter (typically $A_r$) measured in the supporting electrolyte exhibits high sensitivity to standard additions of high-molecular-weight suppressor additive species but low sensitivity to additions of the low-molecular-weight species. Such measurements can be used to define the molecular weight range corresponding to suppressor breakdown contaminants since species that do not adequately suppress the metal deposition rate at the potentials corresponding to the current density levels used in the actual plating process are ineffective as suppressor additives but, at higher concentrations, are likely to degrade the deposit properties. For the PEG additive in typical acid copper sulfate baths, the high and low molecular weight (MW) ranges may be roughly defined as >5000 (suppressor additive) and <2000 (suppressor breakdown contaminants), respectively, with 2000–5000 MW representing an intermediate range. A molecular weight of around 10,000 is typically provided by plating bath suppliers. Alternatively, dilution titration or response curve results obtained for various CVS potential limits may be correlated with the deposit properties (obtained in the laboratory or a production process) to define appropriate potential limits for the suppressor breakdown contaminant analysis of the present invention.

Description of a Preferred Embodiment

In a preferred embodiment of the present invention, the relative concentrations of active suppressor and suppressor breakdown contaminants in an acid copper electroplating bath are determined by CVS dilution titration analyses performed using two different negative electrode potential limits. These potential limits are predetermined to provide good separation for the analyses of the active suppressor and the breakdown contaminants. For the CVS voltammetric measurements, the potential of a rotating platinum disk electrode is cycled relative to a reference electrode between fixed positive and negative potential limits via a potentiostat and a counter electrode. The preferred CVS rate parameter is the integrated copper stripping peak area ($A_r$). Measurements are preferably made at a constant temperature (within $\pm 0.5°$ C.). The dilution titration preferably involves standard addition of known volumes of the plating bath to a known volume of the bath supporting electrolyte. The concentrations of other additives and chloride ion in the plating bath are preferably maintained within the ranges recommended by the bath supplier (for chloride ion, typically 25 to 100 ppm). After each standard addition, sufficient time should be allowed for stirring via the rotating disk electrode (or other means) to provide a homogeneous solution. A preferred endpoint is the volume fraction of added plating bath at which the $A_r$ value is decreased to 50% of the $A_r(0)$ value. The relative concentration of the suppressor breakdown contaminants is preferably expressed as the mathematical difference or ratio of the endpoint volume fractions measured for the two negative electrode potential limits.

Prior to the dilution titration analysis, the potential of the working electrode is preferably cycled (over the potential range used for the analysis) in the bath supporting electrolyte to condition the electrode surface. For both the electrode conditioning and the dilution titration analyses, the potential of the working electrode is preferably cycled until successive $A_r$ values differ by less than a predetermined percentage (typically 0.5%).

Optimum CVS measurement parameters for the method of the present invention depend on the type of acid copper plating bath and the specific additive system. For the suppressor analysis, the negative potential limit may be any value more negative than −0.30 V vs. SSCE but the preferred value is typically between −0.35 and −0.45 V vs. SSCE. For the suppressor breakdown contaminant analysis, any value between 0.0 and −0.3 V vs. SSCE may be used for the negative potential limit but the preferred value is typically between −0.15 and −0.25 V vs. SSCE. Other parameters are typically the same for both analyses. Typical ranges are 100–5000 rpm for the electrode rotation rate, 50–500 mV/s for the potential scan rate, and 1.4 to 1.8 V vs. SSCE for the positive potential limit.

The efficacy of the present invention was demonstrated via CVS dilution titration measurements at a platinum disk electrode (4 mm diameter) rotating at 200 rpm in a typical acid copper sulfate supporting electrolyte (25° C.) containing 75 g/L $CuSO_4 \cdot 5\ H_2O$, 175 g/L $H_2SO_4$, and 50 ppm chloride ion (added as hydrochloric acid). Polyethylene glycols (PEG's) of various known molecular weights (MW) purchased from a chemical supplier (Aldrich Chemical) were added to simulate typical suppressor additives and suppressor breakdown contaminants. Electrolytes were prepared using de-ionized water. CVS measurements were made under potentiostatic control using a Qualilab QL-10® plating bath analyzer (ECI Technology, Inc.). The counter electrode was a stainless steel rod and the reference electrode was a modified silver-silver chloride electrode (SSCE/M) for which the solution in a standard SSCE electrode was replaced with a saturated AgCl solution also containing 0.1 M KCl and 10 volume % sulfuric acid. The working electrode potential was scanned at 300 mV/s between a positive limit of +1.575 V and a negative limit of −0.400 V vs. SSCE/M to detect high-molecular-weight PEG species (suppressor additive) and a negative limit of −0.225 V vs. SSCE/M to also detect low-molecular-weight PEG species (suppressor breakdown contaminants). The endpoint for the dilution titration was the volume fraction of added plating bath at which the $A_r$ value was decreased to 50% of the $A_r(0)$ value (50% suppression endpoint). For $A_r$ measurements, the anodic current was integrated over the potential range from the zero-current potential (at the cathodic-anodic crossover) to 0.55 V vs. SSCE/M. These measurement conditions were also shown to give good results for a variety of commercial acid copper sulfate plating baths, including the Low Acid Viaform™ (Enthone, Inc.), High Acid Viaform™ (Enthone, Inc.) and Ultrafill™ (Shipley, Inc.) baths that are widely used for Damascene plating.

EXAMPLE 1

Dilution titrations with CVS potential limits of −0.400 and −0.225 V vs. SSCE/M were performed for 10 $\mu$M solutions of PEG polymers of different molecular weights. FIG. 1 shows the effect of PEG molecular weight on the endpoint volume fractions for the two potential limits. These data demonstrate that PEG species with molecular weights less than about 1000 have relatively small effects on the dilution titration results for a CVS potential limit of −0.400 (very large endpoint volume fractions), whereas the low-molecular-weight PEG species are readily detected with a −0.225 V potential limit (relatively small endpoint volume fractions). In both cases, the endpoint volume fractions decrease as the molecular weight increases, indicating that the higher molecular weight PEG polymers are more effective at suppressing the copper deposition rate on a per molecule basis. Consequently, cleavage of high molecular weight polymers during copper plating tends to decrease the activity of the suppressor additive. However, polymer chain cleavage produces an increase in the concentrations of lower molecular weight species that may offset their lower activities so that suppressor activity may temporary increase with time after suppressor additions to the plating bath.

Figure 2:
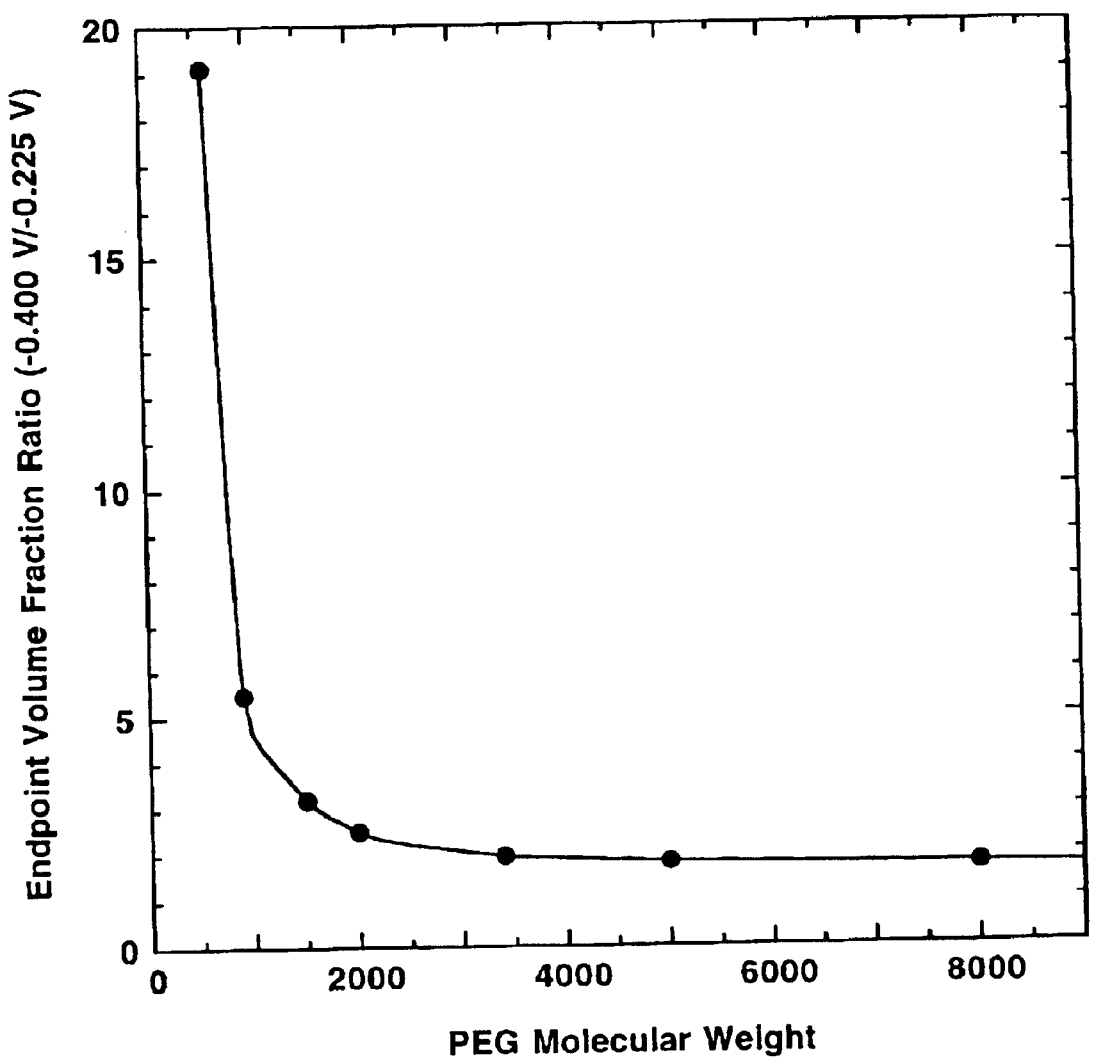
FIG. 2 is a plot of the ratio of the CVS endpoint volume fraction at a negative potential limit of −0.400 V to that at a negative potential limit of −0.225 V vs. SSCE/M as a function of the PEG molecular weight (10 $\mu$M PEG solutions).

FIG. 2 shows the data from FIG. 1 plotted as the ratio of the CVS endpoint volume fraction at a potential limit of −0.400 V to that at a potential limit of −0.225 V as a function of the PEG molecular weight. This plot illustrates that the effect of the PEG molecular weight on the copper electrodeposition rate is continuous rather than discrete, but species with molecular weight below about 1000 are much less effective at suppressing the electrodeposition rate for the −0.400 V potential limit. Consequently, measurements of the copper electrodeposition rate at two negative potentials according to the present invention provides a relative measure of the concentrations of high-molecular-weight species, which are effective suppressor additives, and low-molecular-weight species, which represent bath contaminants. For the electrode potential limits used, the transition between the two types of behavior apparently occurs for PEG molecular weights in the 1000 to 2000 range.

EXAMPLE 2

Figure 3:
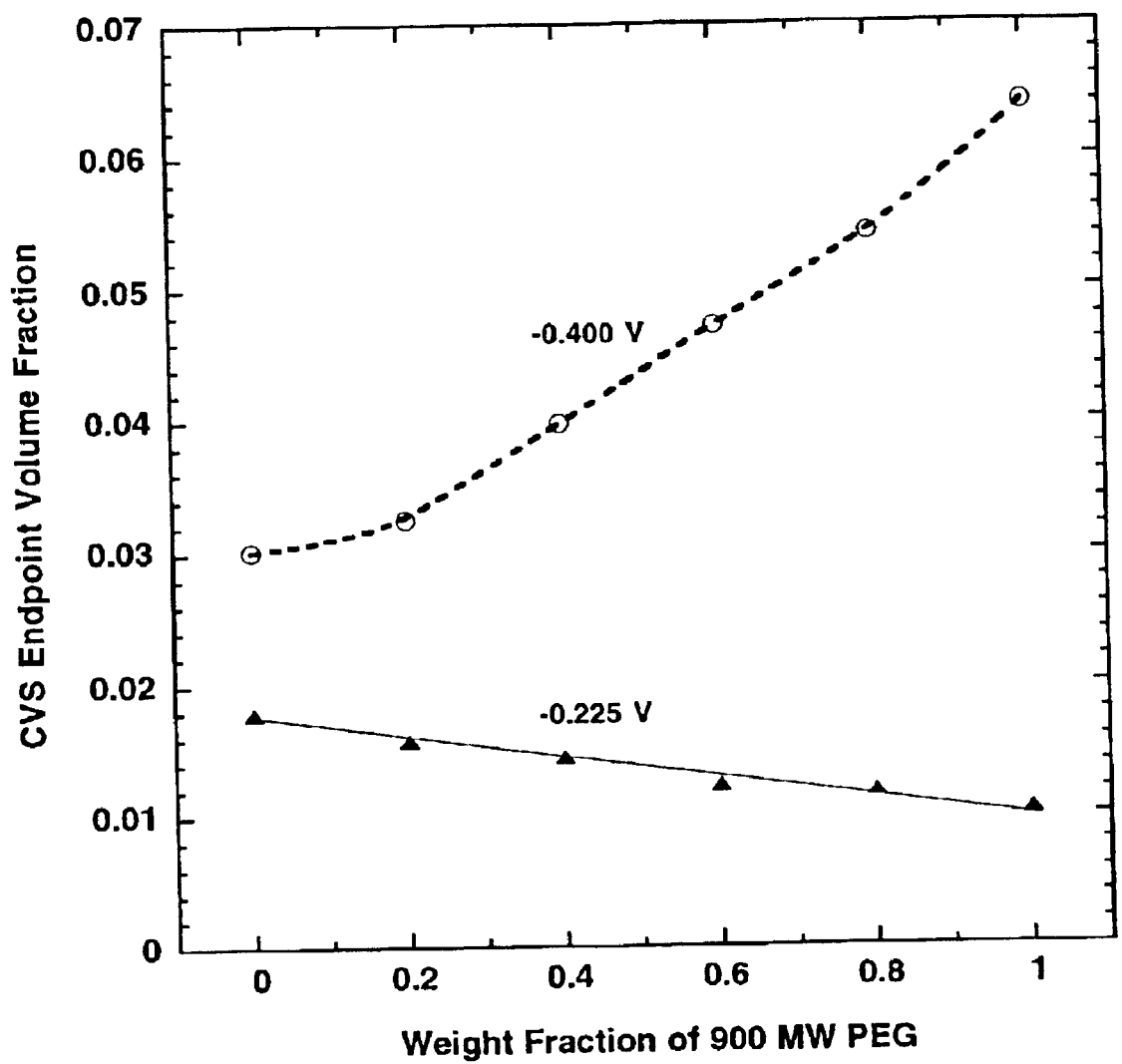
FIG. 3 is a plot of the endpoint volume fraction for 50% suppression of the CVS rate parameter ($A_r$) for negative potential limits of −0.225 and −0.400 V vs. SSCE/M as a function of the weight fraction of 900 MW PEG for mixtures of 900 and 10,000 MW PEG's in test solutions having 1.0 g/L total PEG concentration.

Dilution titrations with CVS potential limits of −0.400 and −0.225 V vs. SSCE/M were performed for solutions containing 1.0 g/L of PEG polymer comprised of mixtures of the 900 and 10,000 MW species. FIG. 3 shows plots of the CVS endpoint volume fractions (measured for the two potential limits) as a function of the weight fraction of the 900 MW species. For the −0.400 V limit, the endpoint volume fraction increases as the fraction of the 900 MW species increases since the concentration of the 10,000 MW species is decreasing and the 900 MW species is relatively inactive as a suppressor for this potential limit. For the −0.225 V limit, the endpoint volume fraction exhibits a slight decrease as the weight fraction of the 900 MW species increases since both PEG polymer species are effective suppressors at this potential limit and the overall PEG molar concentration is increasing.

Figure 4:
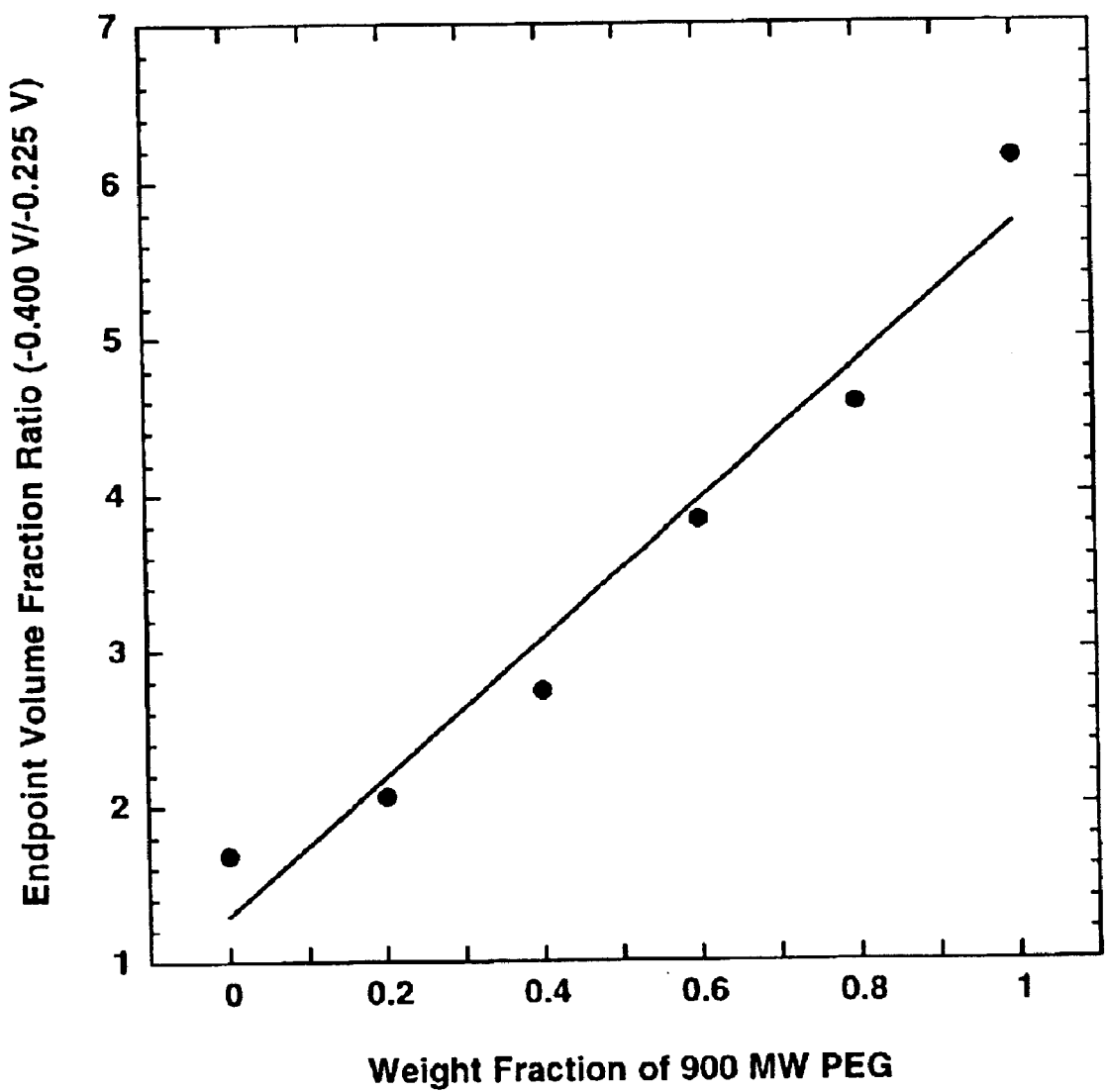
FIG. 4 is a plot of the ratio of the CVS endpoint volume fraction at a negative potential limits of −0.400 to that at a negative potential limit of −0.225 V vs. SSCE/M as a function of the weight fraction of 900 MW PEG for mixtures of 900 and 10,000 MW PEG species in test solutions having 1.0 g/L total PEG concentration.

FIG. 4 shows a plot of the ratio of the endpoint volume fraction for the −0.400 V potential limit to that for the −0.225 V limit as a function of the weight fraction of the 900 MW PEG species. Good sensitivity of this ratio to the relative concentration of the 900 MW species in the presence of the 10,000 MW species is evident. This plot is analogous to a calibration curve for the low-molecular-weight species but is usually not suitable for actual plating baths, which typically contain PEG species having a wide range of molecular weights. In practice, such an endpoint volume fraction ratio for two CVS potential limits provides a reliable relative measure of the concentration of the suppressor breakdown contaminants (low-molecular-weight species) relative to the active suppressor (high-molecular-weight species).

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for measuring the relative concentration of suppressor additive breakdown contaminants in an acid copper plating bath containing a suppressor additive, comprising the steps of:
    determining a first volume fraction of the plating bath added to a plating solution required to reduce a copper electrodeposition rate parameter measured for the plating solution at a first negative electrode potential to a predetermined value;
    determining a second volume fraction of the plating bath added to the plating solution required to reduce the copper electrodeposition rate parameter measured for the plating solution at a second negative electrode potential to the predetermined value; and
    comparing the first volume fraction and the second volume fraction to determine the concentration of the suppressor additive breakdown contaminants relative to the concentration of the suppressor additive.

2. The method of claim 1, wherein the acid copper plating bath comprises anions selected from the group consisting of sulfate, chloride, bromide, iodide, fluoroborate, sulfamate, alkylsulfonate, and mixtures thereof.

3. The method of claim 1, wherein the plating solution is selected from the group consisting of supporting electrolyte and background electrolyte.

4. The method claim 1, wherein the copper electrodeposition rate parameter is measured by a method selected from the group consisting of CVS and CPVS.

5. The method of claim 4, wherein the copper electrodeposition rate parameter is selected from the group consisting of copper stripping peak area, copper stripping peak height, current at a predetermined cathodic potential, integrated current over a predetermined cathodic potential range, and average current over a predetermined cathodic potential range.

6. The method of claim 1, wherein the copper electrodeposition rate parameter is measured by an alternating current (ac) method.

7. The method of claim 1, wherein the first and second negative electrode potentials are fixed potentials.

8. The method of claim 1, wherein the first and second negative electrode potentials are negative potential limits.

9. The method of claim 1, wherein the predetermined value of the copper electrodeposition rate parameter is substantially the minimum value of the copper electrodeposition rate parameter.

10. The method of claim 1, wherein the predetermined value of the copper electrodeposition rate parameter is a predetermined fraction of the sum of the maximum value and the minimum value of the copper electrodeposition rate parameter.

11. The method of claim 1, wherein the predetermined value of the copper electrodeposition rate parameter is a predetermined percentage of the maximum value of the copper electrodeposition rate parameter.

12. The method of claim 1, wherein the step of comparing includes use of a mathematical relationship between the first volume fraction and the second volume fraction.

13. The method of claim 12, wherein the mathematical relationship is selected from the group consisting of difference and ratio.

14. A method for measuring the relative concentration of suppressor additive breakdown contaminants in an acid copper plating bath containing a suppressor additive, comprising the steps of:
    performing a first CVS standard addition analysis using a first negative electrode potential limit to determine a first volume fraction of the plating bath added to a plating solution required to reduce the CVS rate parameter measured for the plating solution to a predetermined value;

performing a second CVS standard addition analysis using a second negative electrode potential limit to determine a second volume fraction of the plating bath added to the plating solution required to reduce the CVS rate parameter measured for the plating solution to the predetermined value; and comparing the first volume fraction and the second volume fraction to determine the concentration of the suppressor additive breakdown contaminants relative to the concentration of the suppressor additive.

15. The method of claim 14, wherein the acid copper plating bath comprises anions selected from the group consisting of sulfate, chloride, bromide, iodide, fluoroborate, sulfamate, alkylsulfonate, and mixtures thereof.

16. The method of claim 14, wherein the plating solution is selected from the group consisting of supporting electrolyte and background electrolyte.

17. The method of claim 14, wherein the standard addition analysis is selected from the group consisting of dilution titration analysis and response curve analysis.

18. The method of claim 14, wherein the CVS rate parameter is selected from the group consisting of copper stripping peak area, copper stripping peak height, current at a predetermined cathodic potential, integrated current over a predetermined cathodic potential range, and average current over a predetermined cathodic potential range.

19. The method of claim 14, wherein the first negative electrode potential limit has a value more negative than −0.30 V versus the SSCE reference electrode, and the second negative electrode potential limit has a value between 0.0 and −0.3 V versus the SSCE reference electrode.

20. The method of claim 14, wherein the predetermined value of the CVS rate parameter is substantially the minimum value.

21. The method of claim 14, wherein the predetermined value of the CVS rate parameter is a predetermined fraction of the sum of the maximum value and the minimum value.

22. The method of claim 14, wherein the predetermined value of the CVS rate parameter is a predetermined percentage of the maximum value of the CVS rate parameter.

23. The method of claim 14, wherein the step of comparing includes use of a mathematical relationship between the first volume fraction and the second volume fraction.

24. The method of claim 23, wherein the mathematical relationship is selected from the group consisting of difference and ratio.

25. A method for measuring the relative concentration of suppressor additive breakdown contaminants in an acid copper sulfate plating bath containing a suppressor additive, comprising the steps of:

performing a first CVS dilution titration analysis using a first negative electrode potential limit to determine a first volume fraction of the plating bath added to a plating solution required to reduce the CVS stripping peak area measured for the plating solution to a predetermined value;

performing a second CVS dilution titration analysis using a second negative electrode potential limit to determine a second volume fraction of the plating bath added to the plating solution required to reduce the CVS stripping peak area measured for the plating solution to the predetermined value; and comparing the first volume fraction and the second volume fraction to determine the concentration of the suppressor additive breakdown contaminants relative to the concentration of the suppressor additive.

26. A method for measuring the relative concentration of suppressor additive breakdown contaminants in a first metal plating bath containing a suppressor additive, comprising the steps of:

determining a first volume fraction of the first metal plating bath added to a second metal plating solution required to reduce a second metal electrodeposition rate parameter measured for the plating solution at a first negative electrode potential to a predetermined value;

determining a second volume fraction of the first plating bath added to the second metal plating solution required to reduce the second metal electrodeposition rate parameter measured for the plating solution at a second negative electrode potential to the predetermined value; and comparing the first volume fraction and the second volume fraction to determine the concentration of the suppressor additive breakdown contaminants relative to the concentration of the suppressor additive.

27. The method of claim 26, wherein at least one of the first and second metals is selected from the group consisting of copper, tin, tin-lead, nickel and cobalt.

* * * * *